(12) United States Patent
Goda et al.

(10) Patent No.: US 6,270,623 B1
(45) Date of Patent: Aug. 7, 2001

(54) METHOD FOR MAKING APERTURED NONWOVEN FABRIC

(75) Inventors: Hiroki Goda; Tomoko Tsuji, both of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/218,437

(22) Filed: Dec. 22, 1998

(30) Foreign Application Priority Data

Dec. 26, 1997 (JP) .................................................. 9-359100

(51) Int. Cl.[7] .................................................. D21F 11/00
(52) U.S. Cl. .................. 162/114; 162/115; 162/109; 19/161.1; 28/104; 28/105; 428/131; 442/408
(58) Field of Search ..................................... 162/114, 115, 162/109; 19/161.1; 28/104, 105; 428/131; 442/408

(56) References Cited

U.S. PATENT DOCUMENTS 3,485,706 * 12/1969 Evans ...................................... 161/72

FOREIGN PATENT DOCUMENTS

| 0 215684 | 3/1987 | (EP) . |
|---|---|---|
| 61-176346 | 8/1961 | (JP) . |
| 61-176346 | 8/1986 | (JP) . |
| 62-69867 | 3/1987 | (JP) . |

\* cited by examiner

Primary Examiner—Stanley S. Silverman
Assistant Examiner—Mark Halpern
(74) Attorney, Agent, or Firm—Baker & Daniels

(57) ABSTRACT

A method for making an apertured nonwoven fabric includes the steps of: obtaining wet sheet from slurry containing 0.5~20% by weight of fibrous component in water, which comprises, in turn, thermoplastic synthetic fibers having a length of 7~30 mm and a fineness of 0.1~0.8 d, and subjecting the wet sheet to a processing for fiber entangling by high velocity water jet streams and to a processing for aperture forming by aperture forming elements having predetermined configurations adapted to be followed by individual fibers.

2 Claims, 3 Drawing Sheets

METHOD FOR MAKING APERTURED NONWOVEN FABRIC

BACKGROUND OF THE INVENTION

This invention relates to a method for making an apertured nonwoven fabric containing thermoplastic synthetic microfibers and being suitable to be used as a liquid-permeable topsheet in disposable body fluids absorbent articles such as disposable diapers or sanitary napkins.

It is known to form a nonwoven fabric comprising the thermoplastic synthetic fibers having a fineness of 1~10 d with liquid-permeable apertures so as to be used as a topsheet in a body fluids absorbent article. An example of the methods for such nonwoven fabric is disclosed in Japanese Patent Application Disclosure Gazettes (Kokai) Nos. Sho 61-176346 and Sho 62-69867, according to which a card web comprising fibers each having a fineness of 1~10 d and a length of approximately 50 mm is subjected to high velocity water jet streams to form a nonwoven fabric. During this processing by the water jet streams, component fibers of a web are partially reoriented around a plurality of projections formed on a surface of support for the web and thereby the nonwoven fabric is formed with a plurality of liquid-permeable apertures corresponding to the respective projections. It is also known to form these liquid-permeable apertures by feeding the nonwoven fabric to a pair of embossing rolls so that the nonwoven fabric may be pierced by a plurality of needle teeth formed on a peripheral surface of one of these embossing rolls.

However, the conventional method for forming the liquid-permeable topsheet with these apertures is often accompanied with an inconvenience such that, when it is attempted to form the apertures each having a diameter of 0.5~5 mm, individual fibers may often extend from the aperture periphery into this aperture, resulting in the indistinctly contoured aperture. Probably, it is for the reason that the individual fibers can not be smoothly reoriented around each of projections. The smaller a diameter of the aperture and/or larger a basis weight of the nonwoven fabric is, the greater this problem becomes serious. While it is obvious that the individual fibers extending into the aperture lead to a substantial reduction of the aperture's diameter, a degree of such reduction is not necessarily uniform. This makes a proper design of the aperture difficult. Accordingly, it is required for the nonwoven fabric used as the liquid-permeable topsheet to have a sufficiently high formability to facilitate formation of the apertures.

SUMMARY OF THE INVENTION

In view of the problem as has been described above, it is an object of the invention to provide a method for making a nonwoven fabric allowing formation of distinctly contoured apertures to be facilitated.

According to the invention, there is provided a method for making an apertured nonwoven fabric containing thermoplastic synthetic microfibers, the method comprising the steps of:

a. obtaining a wet sheet from slurry containing 0.5~20% by weight of thermoplastic synthetic fibers having a length of 7~30 mm and a fineness of 0.1~0.8 d dispersed in water;

b. placing the wet sheet on a support and then subjecting the wet sheet to high velocity water jet streams of 50~200 kgf/cm² for mechanically entangling the fibrous mixture; and c. during the mechanically entangling of the fibrous mixture, forming any one of the wet sheet and dry sheet obtained from the wet sheet with a plurality of apertures each having a diameter of 0.5~5 mm at a total apertured area ratio of 3~60%.

According to one preferred embodiment of the invention, the method for making the apertured nonwoven fabric includes a step of placing the wet sheet on a support provided on a surface thereof with a plurality of projections each having a desired tip configuration and reorienting the component fibers of the wet sheet around the projections under the effect of the high velocity water jet streams. Alternatively, the method for making the apertured nonwoven fabric includes a step of causing a plurality of projections each having a desired tip configuration to pierce the dry sheet in a thickness direction thereof.

According to still another embodiment of the invention, the thermoplastic synthetic fibers comprise melt blown fibers.

DESCRIPTION OF THE PREFERRED EMBODIMENT

Details of an apertured nonwoven fabric and a method for making the apertured nonwoven fabric will be more fully understood from the description given hereunder with reference to the accompanying drawings.

Figure 1:
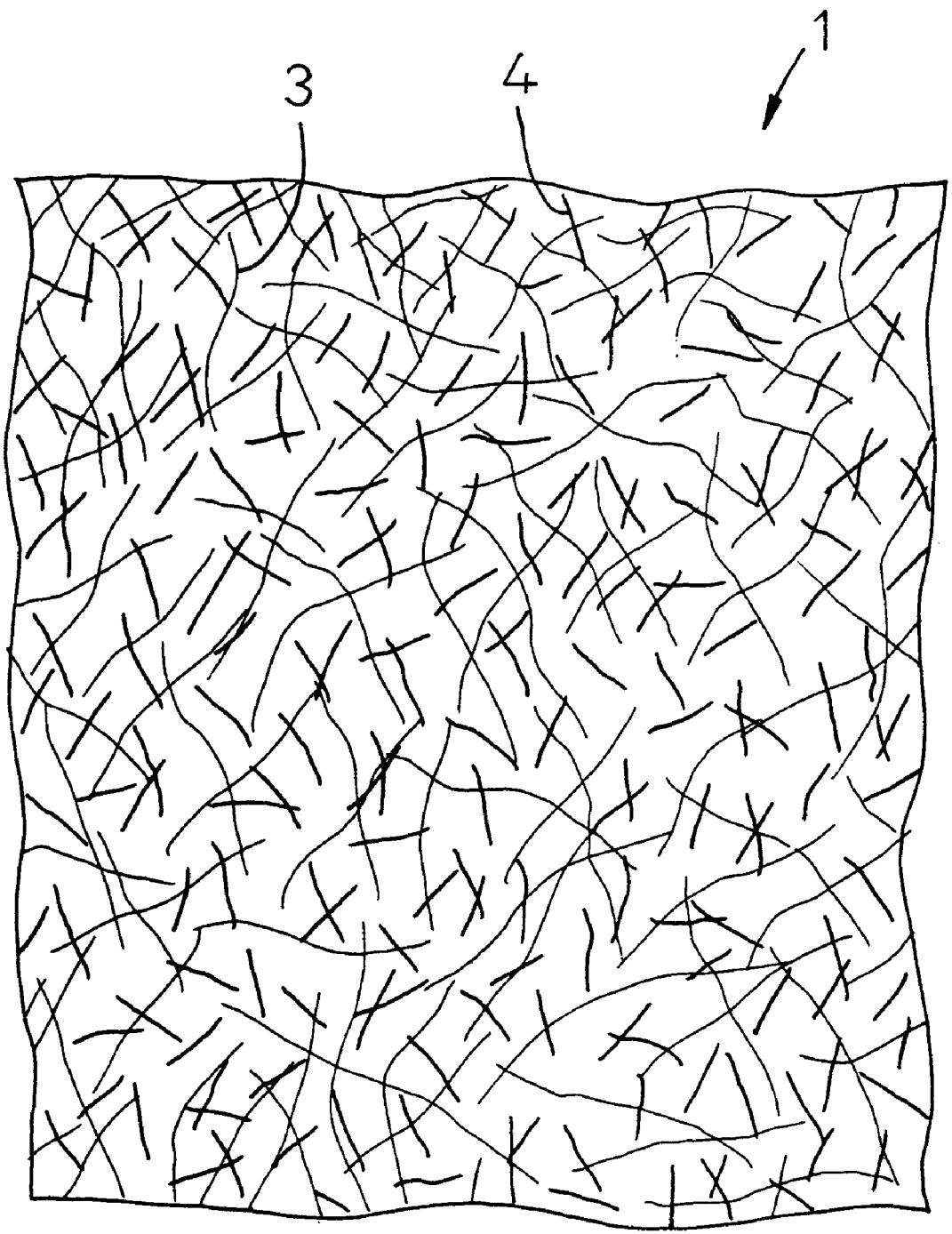
FIG. 1 is a plan view of a nonwoven fabric before apertured.

FIG. 1 is a plan view of a nonwoven fabric 1 before apertured. The nonwoven fabric 1 has a basis weight of 10~80 g/m², and comprises thermoplastic synthetic fibers 3 being 7~30 mm long and as fine as of 0.1~0.8 d, in 90~10% by weight, and pulp fibers 4 (e.g., NBKP), in 10~90% by weight. These fibers 3, 4 are mixed with each other as homogeneously as possible so that they are mechanically entangled to maintain the form of a nonwoven fabric. Individual fibers are randomly distributed or slightly oriented in the machine direction during a manufacturing process of the nonwoven fabric 1 as will be described later. It should be understood that none of binding agents such as poval is employed in making the nonwoven fabric.

Figure 2:
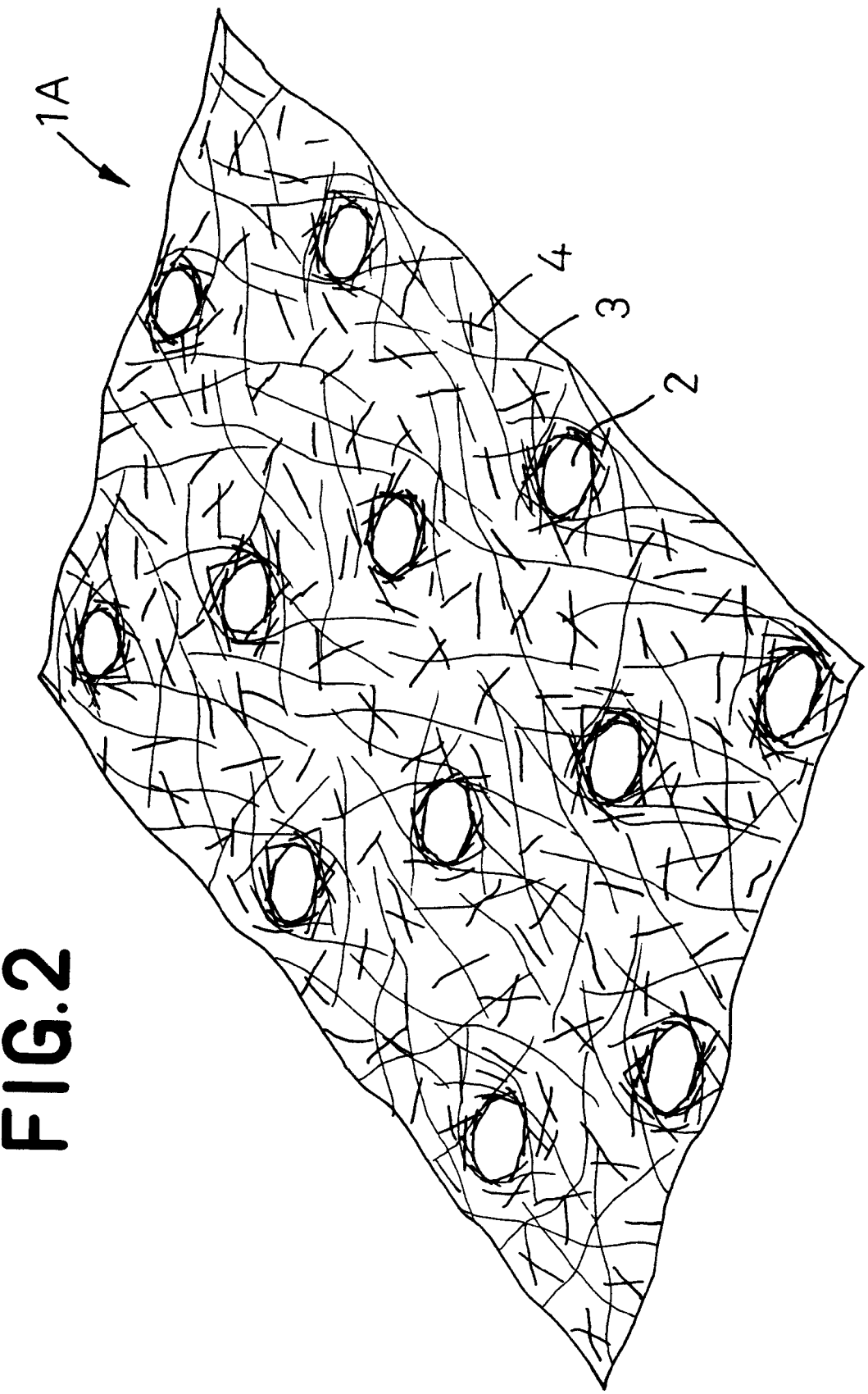
FIG. 2 is a perspective view of an apertured nonwoven fabric.

FIG. 2 is a perspective view of apertured nonwoven fabric 1A. The apertured nonwoven fabric 1A is adapted to be used a liquid-permeable topsheet in body fluids absorbent articles such as disposable diapers, disposable training pants, disposable incontinent pants, sanitary napkins or the like. The apertured nonwoven fabric 1A is obtained by causing the nonwoven fabric 1 of FIG. 1 to be pierced by projections formed on a peripheral surface of an embossing roll. The nonwoven fabric 1 is thus formed with a plurality of liquid-permeable apertures 2 each having a diameter of 0.5~5 mm. A total apertured area ratio, i.e., a ratio between a sum of area occupied by all the apertures 2 and an entire area of the apertured nonwoven fabric 1A is in a range of 3~60%. The synthetic fibers 3 and the pulp fibers 4 extend along the peripheries of the respective apertures 2 and are randomly distributed between each pair of the adjacent apertures 2 just as in the case of FIG. 1.

Figure 3:
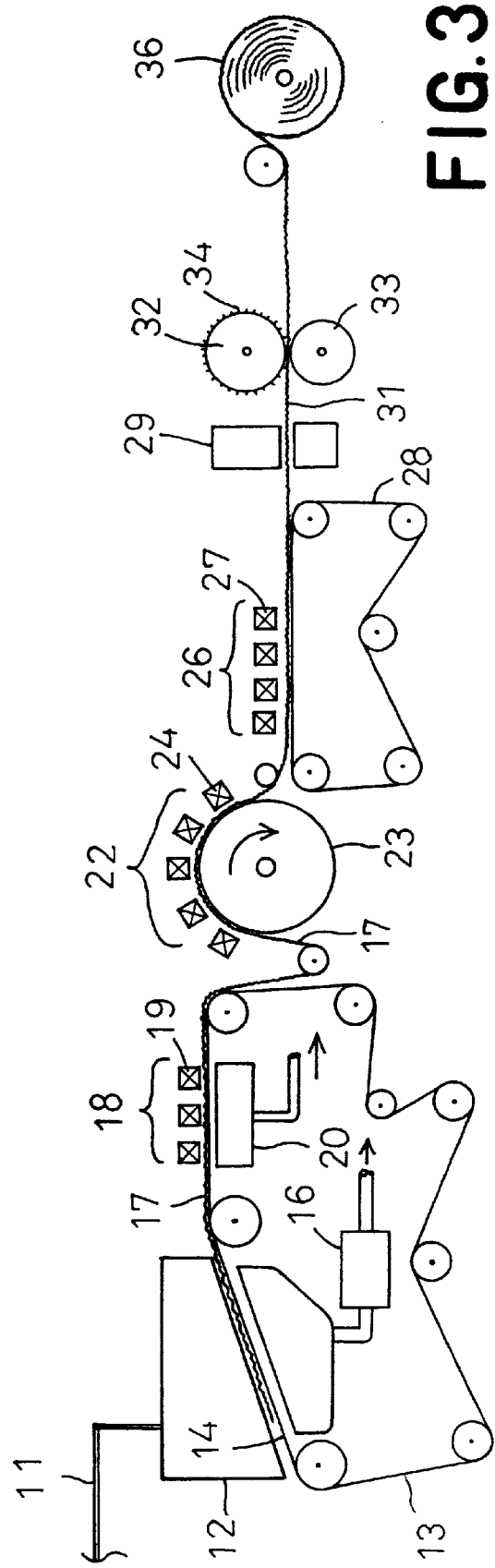
FIG. 3 is a diagram schematically illustrating the steps of a method for making the apertured nonwoven fabric.

FIG. 3 is a diagram exemplarily illustrating the steps of the inventive method for making the nonwoven fabric 1 and the apertured nonwoven fabric. The method starts from the left in FIG. 3. Slurry containing 0.5~20% by weight of the fibrous mixture which comprises, in turn, the thermoplastic synthetic fibers 3 and the pulp fibers 4 at a weight ratio of 10:0~1:9 is supplied through a feed pipe 11 to a slurry tank 12. From the tank 12, slurry is then fed onto a first endless belt 13 in a suction zone 14 in which the endless belt 13 describes a rightward ascending slope. In the suction zone 14, slurry is dehydrated by a vacuum pump 16 and thereby wet sheet 17 is obtained. The wet sheet 17 is then subjected, in a first zone 18, to high velocity water jet streams injected from a first nozzle 19 to stabilize a texture of the wet sheet 17 which is then transferred to a rotary drum 23 installed in a second zone 22. The amount of water injected in the first zone 18 is drawn by a suction mechanism 20. In the second zone 22, the wet sheet 17 supported on a smooth surface of the rotary drum 23 is subjected to high velocity water jet streams injected from a second nozzle 24 to ensure that component fibers of the wet sheet 17 are mechanically entangled together. Now the wet sheet 17 is transferred to a second endless belt 28 and subjected, in a third zone 26, to high velocity water jet streams injected from a third nozzle 27. Thereafter, the wet sheet 17 is dehydrated and dried by dehydrator/drier means 29 to obtain a nonwoven fabric 31. As will be apparent, the nonwoven fabric 31 may be cut into an appropriate size to obtain the nonwoven fabric 1 of FIG. 1. If desired, the nonwoven fabric 31 may be further transported so as to pass between a pair of embossing rolls 32, 33. One of these rolls, is formed on its peripheral surface with forming elements 34 comprising a plurality of conical or pyramidal projections so that a continuous sheet of nonwoven fabric 1A having the apertures 2 as shown in FIG. 2 is obtained as the elements 34 are pressed against the nonwoven fabric 31. The continuous sheet of nonwoven fabric 1A obtained in this manner may be taken up in the form of a roll 36. If necessary, such continuous sheet of nonwoven fabric 1A may be further processed, using an embossing machine or the like, to be formed with a plurality of apertures each having a diameter of 0.5~5 mm.

Along the line of production as has been described above, it is preferably that the second and third zones 22, 26 are also provided with the suction mechanisms 20 similar to those provided in the first zone 18. High velocity water jet streams injected in the first, second and third zones 18, 22, 26 is preferably columnar streams and pressure of these water jet streams is preferably adjusted within a range of 50~200 kgf/cm$^2$. It is not always necessary to use all of the first, second and third zones but any one or more of these zones may be eliminated from the line of production.

Figure 4:
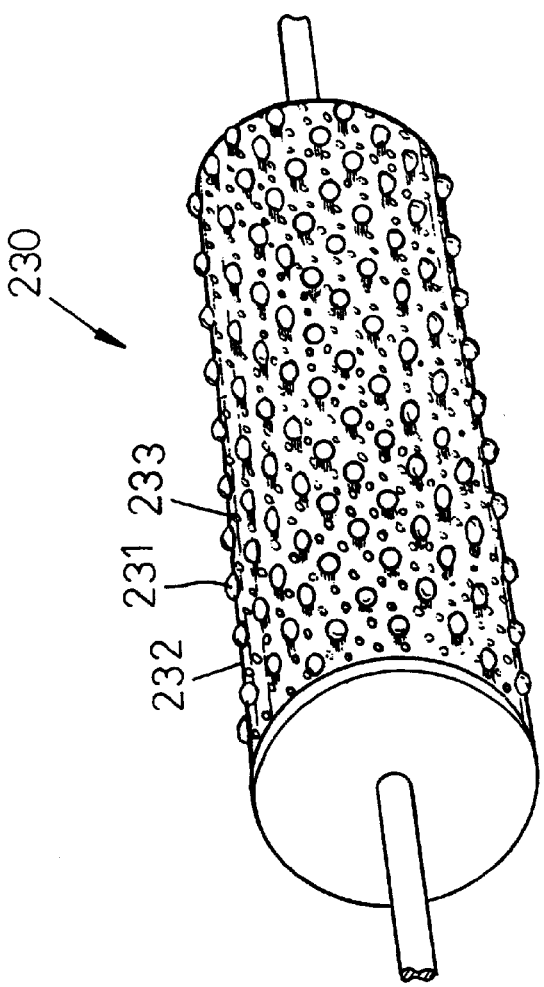
FIG. 4 is a perspective view of a drum used in the method.

FIG. 4 is a perspective view of a drum 230 provided on its.peripheral surface with a flat zone 232, a plurality of projections 231 and a plurality of drain holes 233. The drum 23 having the smooth peripheral surface used in the line of production as illustrated by FIG. 3 may be replaced by this drum 230 to obtain the continuous sheet of nonwoven fabric 1A similar to that shown in FIG. 2. The drum 230 is disclosed in Japanese Patent Application Disclosure Gazettes (Kokai) Nos. Sho 61-176346 and Sho 62-69867. When the high velocity water jet streams impinge against the wet sheet 17 placed on this drum 230, the component fibers 3, 4 are reoriented so as to follow the configurations of the projections 231 and consequently the wet sheet 17 is formed with the apertures 2. The projections 231 are distributed on the drum 230 in conformity with the distribution pattern of the forming elements 34 in FIG. 3. Accordingly, the step of forming the apertures by the pair of rolls 32, 33 in FIG. 3 can be eliminated so far as the drum 230 is employed. The drum 230 may be in the form of a drum having its peripheral surface formed by a mesh screen when knuckles of the mesh screen are used as protuberance forming elements. If desired, the apertured nonwoven fabric 1A obtained by using the drum 230 may be further fed to another pair of embossing rolls and thereby the nonwoven fabric 1A may be additionally formed with a plurality of protuberances.

The nonwoven fabric 1A or 31 obtained by the method illustrated in FIG. 3 can reproduce the configurations of the forming elements 34 with a relatively high precision because both component fibers 3, 4 are relatively short, on one hand, and the synthetic fibers 3 has a relatively low fineness as well as a relatively low rigidity. Once the apertures have been formed, the component fibers 3, 4 remain reoriented substantially without any apprehension that these fibers might extend from the peripheral walls of the respective apertures 2 inwardly. In order to achieve the distinctly contoured apertures 2, such nonwoven fabric 31 preferably has a basis weight of 10~80 g/m$^2$ and the synthetic fibers 3 preferably comprises melt blown fibers.

In the line of production illustrated in FIG. 3, slurry containing relatively short fibers 3, 4 is fed onto the endless belt 13 describing an ascending slope and thereby orientation of these fibers 3, 4 in the direction in which the endless belt 13 travels, i.e., in the machine direction is effectively prevented. As a result, the fibers 3, 4 are slightly oriented in the machine direction or randomly distributed between each pair of the adjacent protuberances 51 on the apertured sheet 1A. In this manner, the apertured sheet 1A is relatively isotropic.

It is possible to form the apertured nonwoven fabric by subjecting a web fed from a card of prior art to the processing steps illustrated in FIG. 3 starting from the first zone 18. However, the fibers which can be effectively processed by the conventional card is limited to that approximately 30 mm or longer and therefore it is difficult for the prior art to make the nonwoven fabric 1 presenting a high formability and thereby facilitating the apertures 2 to be formed as realized by the invention.

The method for making the apertured nonwoven fabric according to the invention basically comprises the step of mechanically entangling the thermoplastic synthetic fibers having a relatively short fibers length as well as a relatively low fineness. Such unique method enables the nonwoven fabric obtained by this method to precisely reproduce the configurations of the forming elements and thereby to form the distinctly contoured apertures. Such nonwoven fabric may be made hydrophilic by mixing the synthetic fibers with the pulp fiber. By utilizing the inventive method for making the nonwoven fabric, it is possible to obtain even from a fibrous material having a fiber length too short to be processed by the conventional card.

What is claimed is:

1. A method for making an apertured nonwoven fabric containing thermoplastic synthetic microfibers, said method comprising the steps of:

a. providing a wet sheet from a slurry containing about 0.5 to 20% by weight of thermoplastic fibers having a length of about 7 to 30 mm and a fineness of about 0.1 to 0.8 d dispersed in water;

b. placing said wet sheet on a support;
c. subjecting said wet sheet to high velocity water jets of about 50 to 200 kgf/cm 2 for mechanically entangling fibers of said wet sheet;
d. drying said wet sheet to form a dry sheet; and
e. forming a plurality of apertures having a diameter of about 0.5 to 5 mm and providing a total apertured area ratio of about 3 to 60% by piercing said dry sheet in a thickness direction with a plurality of projections each having a desired tip configuration.

2. A method according to claim 1, wherein said thermoplastic synthetic fibers comprise melt blown fibers.

* * * * *